United States Patent

Wakai

(10) Patent No.: US 9,936,928 B2
(45) Date of Patent: Apr. 10, 2018

(54) MEDICAL IMAGE PROCESSING APPARATUS AND X-RAY DIAGNOSTIC APPARATUS

(71) Applicant: TOSHIBA MEDICAL SYSTEMS CORPORATION, Otawara-Shi (JP)

(72) Inventor: Satoshi Wakai, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 211 days.

(21) Appl. No.: 15/069,573

(22) Filed: Mar. 14, 2016

(65) Prior Publication Data
US 2016/0345923 A1 Dec. 1, 2016

(30) Foreign Application Priority Data
Jun. 1, 2015 (JP) .................... 2015-111547

(51) Int. Cl.
*A61B 6/02* (2006.01)
*A61B 6/00* (2006.01)

(52) U.S. Cl.
CPC .............. *A61B 6/469* (2013.01); *A61B 6/027* (2013.01); *A61B 6/4441* (2013.01); *A61B 6/487* (2013.01); *A61B 6/503* (2013.01); *A61B 6/504* (2013.01); *A61B 6/547* (2013.01); *A61B 6/466* (2013.01)

(58) Field of Classification Search
CPC ....... A61B 6/027; A61B 6/4441; A61B 6/466; A61B 6/469; A61B 6/487; A61B 6/503; A61B 6/504; A61B 6/547
See application file for complete search history.

(56) References Cited

U.S. PATENT DOCUMENTS

| | | | | |
|---|---|---|---|---|
| 2009/0274271 | A1* | 11/2009 | Pfister | A61B 6/12 378/62 |
| 2010/0014740 | A1 | 1/2010 | Movassaghi et al. | |
| 2011/0276179 | A1* | 11/2011 | Banks | A61B 6/12 700/264 |
| 2016/0166329 | A1* | 6/2016 | Langan | A61B 19/5244 600/424 |

FOREIGN PATENT DOCUMENTS

| | | |
|---|---|---|
| JP | 2009-207683 | 9/2009 |
| JP | 2009-542283 | 12/2009 |
| JP | 5238296 | 7/2013 |
| WO | WO 2008001260 A2 * | 1/2008 ........... A61B 6/4441 |

* cited by examiner

Primary Examiner — Mark R Gaworecki
(74) Attorney, Agent, or Firm — Oblon, McClelland, Maier & Neustadt, L.L.P.

(57) ABSTRACT

A medical image processing apparatus according to the embodiments includes a memory circuitry that stores a program, and a processing circuitry that reads out the program from the memory circuitry and executes the program. The processing circuitry sets a region of interest to be observed and a region of non-interest that is different from the region of interest based on volume data, and determines a trajectory of an arm that holds an X-ray irradiator that irradiates X-rays and a detector that detects the irradiated X-rays based on a relative positional relationship between the region of interest and the region of non-interest.

18 Claims, 13 Drawing Sheets

MEDICAL IMAGE PROCESSING APPARATUS AND X-RAY DIAGNOSTIC APPARATUS

CROSS-REFERENCE TO RELATED APPLICATION

This application is based upon and claims the benefit of priority from Japanese Patent Application No. 2015-111547, filed on Jun. 1, 2015, the entire contents of which are incorporated herein by reference.

FIELD

Embodiments of the present invention relate to a medical image processing apparatus and an X-ray diagnostic apparatus.

BACKGROUND

In recent years, development relating to angiography apparatuses that capture images of blood vessels is being actively pursued. In the case of capturing images of, for example, the coronary arteries using an angiography apparatus, the angiography apparatus extracts a coronary artery region that is a vascular region. The coronary arteries are then extracted from the coronary artery region, and fluoroscopy or imaging using a contrast medium is performed with respect to the coronary arteries.

The coronary arteries are arteries that supply oxygen and nutrients to the cardiac muscle, and that branch from the coronary artery sinus of the ascending aorta. The coronary artery sinus has three dilations which are in the region of origin of the ascending aorta, namely, the right coronary artery sinus, the left coronary artery sinus and the non-coronary artery sinus, and includes the aortic valve that is constituted by three valve cusps, namely, the right coronary cusp, the left coronary cusp and the non-coronary cusp. The right coronary artery branches via the right coronary cusp from the right coronary artery sinus. The left coronary artery branches via the left coronary cusp from the left coronary artery sinus.

Although, from an anatomical viewpoint, the structure of the heart is the same structure in terms of a physical structure in humans, in practice the form thereof differs depending on the individual patient (object). Therefore, examination and medical treatment that is adapted to the respective forms of individual patients is important.

On the other hand, as an angiography apparatus that performs coronary artery intervention, that is, PCI (percutaneous coronary intervention), an X-ray diagnostic apparatus is available that performs rotational imaging using a C-arm.

In the case of using an X-ray diagnostic apparatus to capture images of the coronary arteries, as described above, although the structure of the coronary arteries or the structure of the heart are the same structures for each person from an anatomical viewpoint, the actual shapes thereof differ for each individual patient.

Therefore, when performing fluoroscopy or imaging using an X-ray diagnostic apparatus, in the case of using a trajectory for imaging that is previously set as an initial setting or standard setting, it is necessary to adjust the trajectory of the C-arm to suit the individual patient. That is, when performing imaging of the coronary arteries of a patient, even if the standard trajectory of the C-arm that is set in advance as a standard setting is provided, it is necessary to perform adjustment to adapt to the shape of the coronary arteries of the patient as well as to the manner in which the observation site is to be viewed. Thus, it is necessary to carry out imaging to perform such adjustment, and consequently the patient is exposed to X-rays also at the time of adjusting the trajectory, in addition to the X-ray exposure at the time of treatment. Further, it is necessary to check the captured images one frame at a time when adjusting the trajectory, and it requires time and labor to set the optimal trajectory.

In addition, not only does it require time and labor to set the optimal trajectory, cases can also arise in which the trajectory that is set is not necessarily the optimal trajectory.

DETAILED DESCRIPTION

A medical image processing apparatus according to the present embodiments includes a memory circuitry configured to store a program, and a processing circuitry configured to read out the program from the memory circuitry and execute the program; wherein the processing circuitry is configured to: set a region of interest to be observed and a region of non-interest that is different to the region of interest based on volume data; and determine a trajectory of an arm that holds an X-ray irradiator configured to irradiate X-rays and a detector configured to detect the X-rays that are irradiated, based on a relative positional relationship between the region of interest and the region of non-interest.

First Embodiment

Hereunder, an embodiment of an X-ray diagnostic apparatus that is equipped with a medical image processing apparatus according to a first embodiment will be described with reference to the accompanying drawings.

Figure 1:
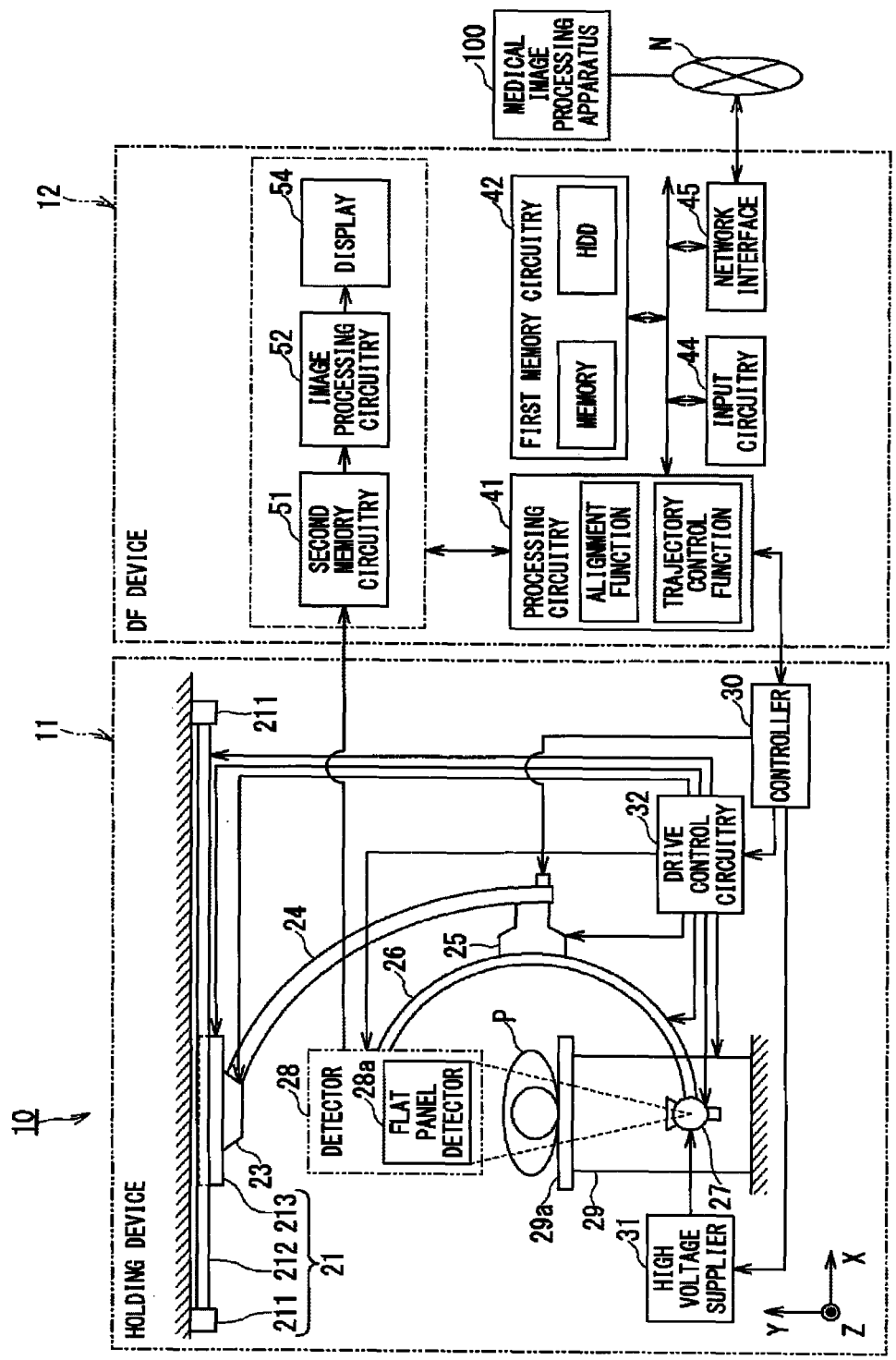
FIG. 1 is a schematic diagram illustrating the hardware configuration of an X-ray diagnostic apparatus of a first embodiment.
Figure 2:
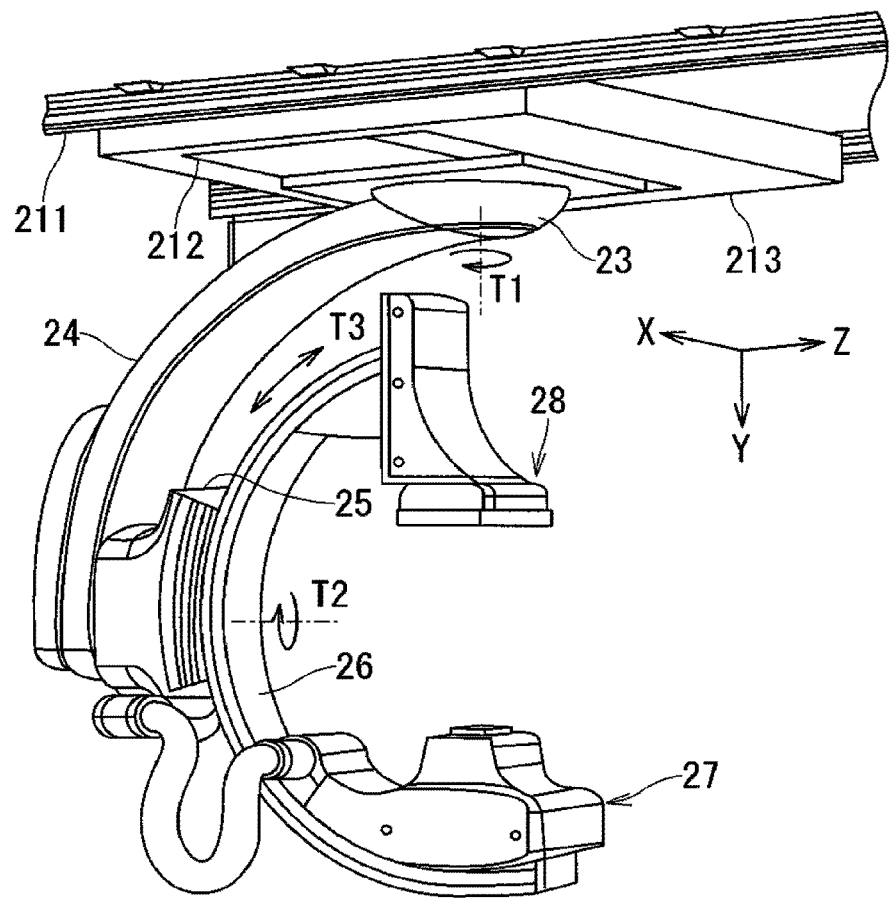
FIG. 2 is a perspective view illustrating the external configuration of a holding device in the X-ray diagnostic apparatus of the first embodiment.

FIG. 1 is a schematic diagram illustrating the hardware configuration of an X-ray diagnostic apparatus 10 of the first embodiment. FIG. 2 is a perspective view illustrating the external configuration of a holding device 11 in the X-ray diagnostic apparatus 10 of the first embodiment.

FIG. 1 illustrates the X-ray diagnostic apparatus 10 that is equipped with a ceiling-traveling C-arm of the first embodiment. The X-ray diagnostic apparatus 10 has a holding device 11, a DF (digital fluorography) device 12 and a medical image processing apparatus 100. The holding device 11 and the DF device 12 are generally installed in an examination room or treatment room.

Note that, the X-ray diagnostic apparatus 10 according to the first embodiment is not limited to an X-ray diagnostic apparatus equipped with a ceiling-traveling C-arm, and may be an X-ray diagnostic apparatus equipped with a floor-traveling C-arm, or may be an X-ray diagnostic apparatus equipped with a floor-standing C-arm. Further, although the X-ray diagnostic apparatus 10 according to the first embodiment is described by adopting an apparatus equipped with a C-arm as one example, the present invention is not limited thereto. For example, the X-ray diagnostic apparatus 10 may be of a form in which an X-ray irradiator and an X-ray detector are held by respectively independent arms.

The holding device 11 has a sliding mechanism 21, a vertical axis rotation mechanism 23, a suspension arm 24, a C-arm turning mechanism 25, a C-arm 26, an X-ray irradiator 27, a detector 28, a bed 29, a controller 30, a high voltage supplier 31 and a drive control circuitry 32.

The sliding mechanism 21 has a Z-axis direction rail 211, an X-axis direction rail 212 and a dolly 213. The sliding mechanism 21 causes the vertical axis rotation mechanism 23, the suspension arm 24, the C-arm turning mechanism 25, the C-arm 26, the X-ray irradiator 27 and the detector 28 to slide integrally in the horizontal direction in accordance with control by the controller 30 via the drive control circuitry 32.

The Z-axis direction rail 211 is extended in the Z-axis direction (the longitudinal axis direction of a top table 29a), and is supported by the ceiling.

The X-axis direction rail 212 is extended in the X-axis direction (short axis direction of the top table 29a), and is supported by the Z-axis direction rail 211 via rollers (not shown) at both ends thereof. The X-axis direction rail 212 is moved in the Z-axis direction on the Z-axis direction rail 211 in accordance with control by the controller 30 via the drive control circuitry 32.

The dolly 213 is supported by the X-axis direction rail 212 via rollers (not shown). The dolly 213 is moved in the X-axis direction on the X-axis direction rail 212 in accordance with control by the controller 30 via the drive control circuitry 32.

The X-axis direction rail 212 that supports the dolly 213 is movable in the Z-axis direction on the Z-axis direction rail 211, and the dolly 213 is movable in the X-axis direction on the X-axis direction rail 212. Consequently, the dolly 213 is movable in horizontal direction (X-axis direction and Z-axis direction) in the examination room.

The vertical axis rotation mechanism 23 is rotationally supported by the dolly 213. In accordance with control by the controller 30 via the drive control circuitry 32, the vertical axis rotation mechanism 23 causes the suspension arm 24, the C-arm turning mechanism 25, the C-arm 26, the X-ray irradiator 27 and the detector 28 to rotate integrally in a vertical axis rotation direction T1 (see FIG. 2)

The suspension arm 24 is supported by the vertical axis rotation mechanism 23.

The C-arm turning mechanism 25 is rotatably supported by the suspension arm 24. In accordance with control by the controller 30 via the drive control circuitry 32, the C-arm turning mechanism 25 causes the C-arm 26, the X-ray irradiator 27 and the detector 28 to rotate integrally in a rotation direction T2 with respect to the suspension arm 24 (see FIG. 2).

The C-arm 26 is supported by the C-arm turning mechanism 25, and causes the X-ray irradiator 27 and the detector 28 to be disposed at opposing positions that are centered on an object P (patient P). A rail (not shown) is provided on the back or a side of the C-arm 26. In accordance with control by the controller 30 via the drive control circuitry 32, the C-arm 26 causes the X-ray irradiator 27 and the detector 28 to move integrally in an arc direction T3 (see FIG. 2) of the C-arm 26 along an arc locus, through the rail that is sandwiched by the C-arm turning mechanism 25 and the C-arm 26.

The X-ray irradiator 27 is provided at one end of the C-arm 26. The X-ray irradiator 27 is provided so as to be capable of forward and backward movement in accordance with control by the controller 30 via the drive control circuitry 32. The X-ray irradiator 27 has an X-ray tube, and upon receiving a supply of high voltage power from the high voltage supplier 31, irradiates X-rays towards a predetermined site of the object P in accordance with the condition of the high voltage power. In the X-ray irradiator 27, an X-ray irradiation field aperture that is constituted by a plurality of lead blades, and a compensating filter that is formed of silicon rubber or the like and that attenuates a predetermined amount of irradiation X-rays to prevent halation and the like are provided on the X-ray emission side.

The detector 28 is provided at a position on the opposite side to the emitting side of the X-ray irradiator 27, that is a position at the other end of the C-arm 26. The detector 28 is provided so as to be capable of forward and backward movement in accordance with control by the controller 30 via the drive control circuitry 32. The detector 28 has a flat panel detector (FPD) 28a, and detects X-rays by means of detecting elements that are two-dimensionally arranged, and converts detected X-rays into digital signals for each pixel.

Note that the detector 28 may be, for example, an I. I. (image intensifier)-TV system. In such a case, the detector 28 may include an I. I., a TV camera and an A/D (analog to digital) conversion circuit. Thus, it is sufficient that the detector 28 can at least detect X-rays transmitted through the object P or that are directly incident thereon.

The bed 29 is installed on the floor surface, and supports a top table (catheter table) 29a. In accordance with control by the controller 30 via the drive control circuitry 32, the bed 29 moves the top table 29a in the horizontal directions (X- and Z-axis directions) and the vertical direction (Y-axis direction), and also causes the top table 29a to perform a rolling motion. The top table 29a is configured to be capable of moving and rolling in a state in which the object P is lying thereon. Note that although in this case an example is described in which the holding device 11 is an under-tube type in which the X-ray irradiator 27 is located below the top table 29a, the holding device 11 may also be an over-tube type in which the X-ray irradiator 27 is located above the top table 29a.

The controller 30 includes a CPU (Central Processing Unit) and a memory that are not shown in the drawings. The controller 30 controls operations of the high voltage supplier 31 and the drive control circuitry 32 and the like. The controller 30 controls the drive control circuitry 32 that drives the bed 29 and the top table 29a, and also calculates positional information of the bed 29 that shows the position of the bed 29, and positional information of the top table 29a that shows the position of the top table 29a.

The high voltage supplier 31 supplies high voltage power to the X-ray irradiator 27 in accordance with control of the controller 30.

The drive control circuitry 32 drives the sliding mechanism 21, the vertical axis rotation mechanism 23, the C-arm turning mechanism 25, the C-arm 26, the X-ray irradiator 27, the detector 28 and the top table 29a of the bed 29, respectively, in accordance with control of the controller 30.

The DF device 12 has a computer-based configuration, and is capable of intercommunication with a network N such as a backbone LAN (local area network) of a hospital. The DF device 12 has hardware such as a processing circuitry 41 that includes a processor, a first memory circuitry 42, an input circuitry 44, a network interface 45, a second memory circuitry 51, an image processing circuitry 52 and a display 54. The processing circuitry 41 is interconnected to each hardware component constituting the DF device 12 via a bus as a common signal transmission line. Note that, in some cases the DF device 12 also includes a drive for a recording medium (not shown).

Further, the DF device 12 is connected via the network N to the medical image processing apparatus 100. The medical image processing apparatus 100 generates an optimal trajectory map for controlling rotational driving of the C-arm 26 that is described later. The DF device 12 acquires an optimal trajectory map that is generated by the medical image processing apparatus 100.

Hereunder, although as one example the present embodiment is configured to generate an optimal trajectory map by means of the medical image processing apparatus 100, according to the present embodiment a configuration may also be adopted in which, for example, the respective functions of the medical image processing apparatus 100 are incorporated into the DF device 12, and the DF device 12 is configured to generate an optimal trajectory map.

Upon a signal from an input device being inputted from the input circuitry 44 by an operation by a physician or a technician or the like, the processing circuitry 41 reads out a program that is stored in the memory of the first memory circuitry 42 and executes the program. Alternatively, the processing circuitry 41 loads into the memory a program that is stored on a HDD (hard disk drive) of the first memory circuitry 42, a program that is transferred from the network N and received with the network interface 45 and installed on the HDD, or a program that is read out from a recording medium that is inserted into a drive for a recording medium (not shown) and installed on the HDD or the like, and executes the relevant program.

An optimal trajectory map for a rotational trajectory of the C-arm 26 that is generated by the medical image processing apparatus 100 is stored in the memory or the HDD of the first memory circuitry 42 via the network N.

The processing circuitry 41 reads out a program for executing an alignment function and a trajectory control function from the first memory circuitry 42, and executes the alignment function and the trajectory control function.

The term "alignment function" refers to a function that performs alignment between a three-dimensional image that is used when generating an optimal trajectory map and an image that is captured with the present apparatus (X-ray diagnostic apparatus 10). For example, the alignment function is configured to detect a difference (displacement amount) between a three-dimensional image that is used when generating an optimal trajectory map and an image that is captured with the X-ray diagnostic apparatus 10, and to correct the trajectory of the optimal trajectory map, that is, the rotational trajectory of the C-arm 26 using the detected difference (displacement amount). Note that, the X-ray diagnostic apparatus 10 captures images of the object from a plurality of directions and performs alignment between captured images and three-dimensional images.

The term "trajectory control function" refers to a function that controls the rotational trajectory of the C-arm 26 in accordance with the corrected optimal trajectory map.

The first memory circuitry 42 includes, as memories, a ROM (read only memory) and a RAM (random access memory) or the like. The memories store data for IPL (initial program loading) and BIOS (basic input/output system), and are used as a work memory of the processing circuitry 41 or to temporarily store data.

The first memory circuitry 42 includes the HDD. The HDD stores programs (also including an OS (operating system) in addition to application programs) that are installed on the DF device 12, and data. Further, the OS can be caused to provide a GUI (graphical user interface) that uses a large amount of graphics to display information to a surgeon, and with which basic operations can be performed by means of the input circuitry 44.

The input circuitry 44 is a circuitry for inputting a signal from an input device such as a pointing device (mouse or the like) or keyboard that can be operated by an operator. In this case, the input device itself is also included in the input circuitry 44. In the present embodiment, an input signal in accordance with an operation is sent from the input circuitry 44 to the processing circuitry 41.

The term "processor" used in the above description refers to, for example, a dedicated or general purpose CPU (central processing unit) or GPU (graphics processing unit), or to a circuit such as an application specific integrated circuit (ASIC), a programmable logic device (for example, a simple programmable logic device (SPLD), a complex programmable logic device (CPLD) and a field programmable gate array (FPGA)). Although a case in which there is one processor (the processing circuitry 41) is exemplified in FIG. 1, the number of processors may also be two or more. The processor implements various functions by reading out and executing a program that is stored in the first memory circuitry 42 or that is directly incorporated into the circuitry of the processor. In a case where a plurality of processors are provided, the first memory circuitry 42 that stores a program may be provided individually for each processor, or the first memory circuitry 42 shown in FIG. 1 may store programs corresponding to the functions of the respective processors.

The network interface 45 carries out communication control according to the respective standards. The network interface 45 has, for example, a function that can connect to the network N via a telephone line or dedicated line. Since the DF device 12 can connect to the network N through the network interface 45, the DF device 12 can perform data communication with the medical image processing apparatus 100.

The second memory circuitry 51 stores projection data that is output from an A/D conversion circuit of the detector 28 of the holding device 11 in accordance with control of the processing circuitry 41. Further, in accordance with control of the processing circuitry 41, the second memory circuitry 51 also stores as data a fluoroscopic image and a captured image that are output from the image processing circuitry 52. The second memory circuitry 51 stores a fluoroscopic image or a captured image before image processing is performing thereon (a so-called "original image"), and whenever an image is to be displayed on the display 54, required image processing is performed each time in the image processing circuitry 52.

In accordance with control of the processing circuitry 41, the image processing circuitry 52 generates data of a fluoroscopic image and a captured image (DA (digital angiography) image) based on projection data that is stored in the second memory circuitry 51. The image processing circuitry 52 also performs image processing with respect to a fluoroscopic image and a captured image that are stored in the second memory circuitry 51. Enlargement/gradation/spatial filter processing with respect to data, minimum value/maximum value trace processing of data accumulated in time series, and addition processing for removing noise may be mentioned as examples of the image processing. Note that, after undergoing image processing by the image processing circuitry 52, the data is output to the display 54 and is also stored once more in the second memory circuitry 51.

In accordance with control of the processing circuitry 41, the display 54 synthesizes examination information (character information and gradations and the like of parameters) such as the patient name with data of the fluoroscopic image and captured image that is generated by the image processing circuitry 52, and after subjecting the synthesized signal to D/A (digital to analog) conversion, displays the converted signal as a video signal. The display 54 includes a live monitor that performs live display of a fluoroscopic image and a captured image that are output from the image processing circuitry 52, or a reference monitor for displaying as a still image a captured image that is output from the image processing circuitry 52 or for displaying a reproduced moving image, or a system monitor for displaying data for switching the FOV (field of view) or data for mainly performing control of the holding device 11 or the like.

Next, the configuration and operations of the medical image processing apparatus 100 will be described.

Figure 3:
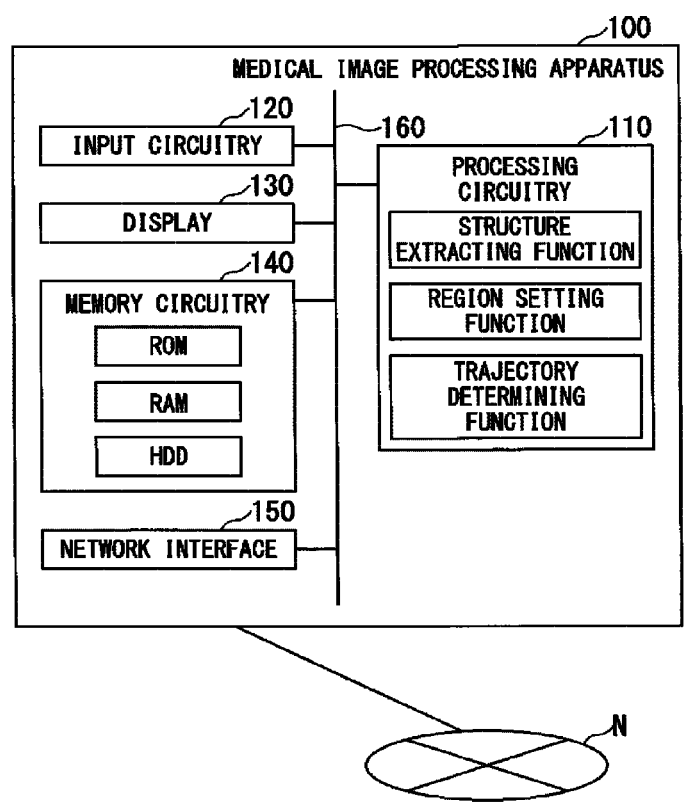
FIG. 3 is a hardware block diagram illustrating the configuration of a medical image processing apparatus of the first embodiment.

FIG. 3 is a hardware block diagram illustrating the configuration of the medical image processing apparatus 100 of the first embodiment. In the present embodiment, the medical image processing apparatus 100 generates an optimal trajectory map for controlling the rotational trajectory of the C-arm 26. Hereunder, a configuration that enables the medical image processing apparatus 100 to generate an optimal trajectory map will be described.

The medical image processing apparatus 100 includes a processing circuitry 110, an input circuitry 120, a display 130, a memory circuitry 140, a network interface 150 and an internal bus 160.

The processing circuitry 110 is a processor that realizes a function corresponding to a program by reading out the program from the memory (memory circuitry 140) and executing the program. In other words, the processing circuitry 110 (processor) can read out a program and realize a structure extracting function, a region setting function and a trajectory determining function.

The structure extracting function is a function that extracts an anatomical structure from volume data. In the present embodiment, for example, a coronary artery region is extracted as a three-dimensional anatomical structure based on three-dimensional image data (volume data). Here, the term "volume data" refers to three-dimensional data of the same patient that is acquired with an X-ray CT (computed tomography) apparatus or an MRI (magnetic resonance imaging) apparatus.

The region setting function is a function that, based on volume data, sets a region of interest to be observed and a region of non-interest which is different from the region of interest. In the present embodiment, for example, a region of interest and a region of non-interest can be set in an extracted anatomical structure. The region setting function, for example, sets the right coronary artery as a region of interest, and sets the left anterior descending coronary artery and the left circumflex coronary as regions of non-interest.

The trajectory determining function is a function that, based on a relative positional relationship between a region of interest and a region of non-interest, determines a trajectory of the C-arm 26 that holds the X-ray irradiator 27 that irradiates X-rays and the detector 28 that detects irradiated X-rays. Note that, information relating to the trajectory of the C-arm 26 that is determined in this case by the trajectory determining function is the aforementioned optimal trajectory map.

The term "processor" used in the above description refers to, as described above, a dedicated or general purpose CPU or to a circuit such as an application specific integrated circuit, a programmable logic device, a complex programmable logic device and a field programmable gate array or the like. Although a case in which there is one processor (the processing circuitry 110) is exemplified in FIG. 3, the number of processors may also be two or more.

The input circuitry 120 is a circuitry for inputting a signal from an input device such as a pointing device (mouse or the like) or keyboard that can be operated by an operator. In this case, the input device itself is also included in the input circuitry 120. In the present embodiment, an input signal in accordance with an operation is sent from the input circuitry 120 to the processing circuitry 110.

The display 130 includes an unshown image synthesizing circuit, VRAM (video random access memory) and screen and the like. The image synthesizing circuit generates synthesized data obtained by synthesizing character data having various parameters or the like with image data. The VRAM expands the synthesized data on the display. The display 130 is constituted by a liquid crystal display, a CRT (cathode ray tube) or the like, and displays images.

The memory circuitry 140 is a memory device including a ROM, a RAM and a HDD or the like. The memory circuitry 140 stores IPL, BIOS and data, and is used as a work memory of the processing circuitry 110 or when temporarily storing data. The HDD is a memory device that stores programs and data installed in the medical image processing apparatus 100.

The memory circuitry 140 stores volume data in the RAM or HDD. According to the present embodiment, as one example of the volume data, three-dimensional image data that is capable of two-dimensionally displaying a three-dimensional image is stored. The three-dimensional image data may be acquired from an external device via the network N, and a configuration may also be adopted in which an imaging function is provided in the medical image processing apparatus 100 to enable the medical image processing apparatus 100 to generate three-dimensional image data.

The network interface 150 performs communication control in accordance with communication standards, and for example has a function that connects the medical image processing apparatus 100 to the network N via a telephone line or dedicated line or the like.

The internal bus 160 is connected to each component so that the medical image processing apparatus 100 is subjected to overall control by the processing circuitry 110.

Note that, the processing circuitry 110 of the medical image processing apparatus 100 may be configured to be equipped with the function for generating a fluoroscopic image of the image processing circuitry 52 that the DF device 12 is equipped with, and the alignment function and the trajectory control function of the processing circuitry 41 that the DF device 12 is equipped with, instead of or in addition to the DF device 12 being equipped with these functions. In this case, it is possible for the processing circuitry 110 of the medical image processing apparatus 100 to directly control the trajectory of the C-arm 26. Further, in addition to controlling the rotational trajectory of the C-arm 26 in accordance with the determined trajectory of the C-arm 26, the processing circuitry 110 of the medical image processing apparatus 100 can generate a fluoroscopic image while the C-arm 26 is being rotated. Furthermore, the processing circuitry 110 can display the generated fluoroscopic image on the display 130 of the medical image processing apparatus 100.

Optimal Trajectory Map Generation Processing

Next, a method by which the medical image processing apparatus 100 of the first embodiment generates an optimal trajectory map and an optimal trajectory map will be described using the flowchart illustrated in FIG. 4 while referring to FIG. 3. Note that, the term "optimal trajectory map" refers to information that shows an optimal trajectory of the C-arm 26 in three dimensions.

Figure 4:
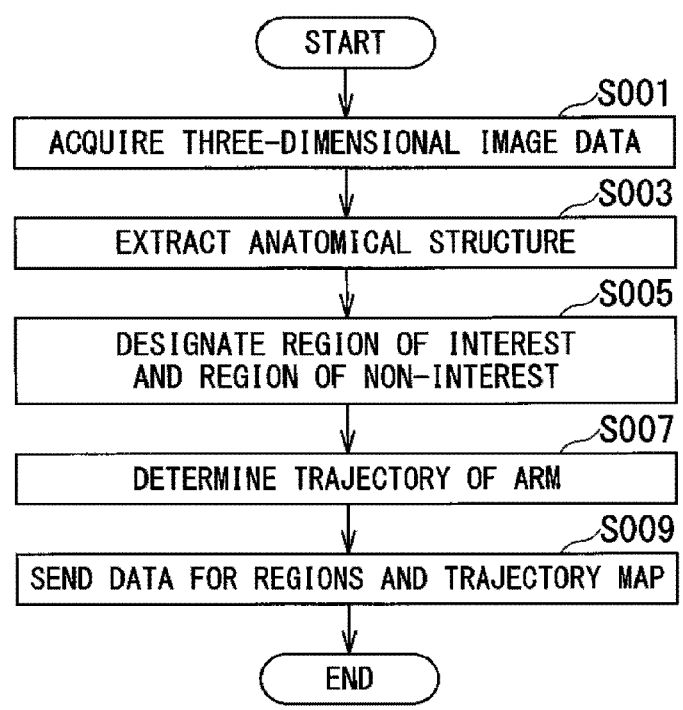
FIG. 4 is a flowchart illustrating processing with which the medical image processing apparatus according to the first embodiment automatically generates an optimal rotational trajectory of a C-arm when imaging coronary arteries of a patient.

FIG. 4 is a flowchart illustrating processing in which the medical image processing apparatus 100 according to the first embodiment automatically generates an optimal rotational trajectory of the C-arm 26 at a time of imaging the coronary arteries of the patient P.

First, the processing circuitry 110 acquires three-dimensional image data that is volume data from the memory circuitry 140 (step S001). In the present embodiment, volume data generated by an X-ray CT apparatus or an MRI apparatus can be used, and the present embodiment does not depend on a modality.

Note that, the volume data is data that is previously acquired from the same patient that is the patient to be imaged using the present apparatus (X-ray diagnostic apparatus 10). The volume data may be previously stored in the memory circuitry 140 as described above, or may be acquired from a modality device that performed imaging to generate the volume data or from an external image server via the network N.

Figure 5A:
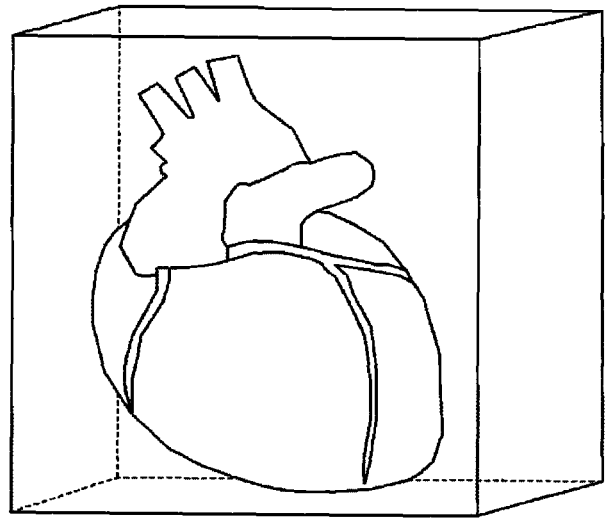
FIG. 5A is an explanatory view in which three-dimensional image data including a coronary artery region that a processing circuitry according to the present embodiment acquired from a memory circuitry is illustrated as an example.

FIG. 5A is a view that illustrates an example of three-dimensional image data including a coronary artery region that the processing circuitry 110 according to the present embodiment acquired from the memory circuitry 140.

For example, as shown in FIG. 5A, the processing circuitry 110 acquires three-dimensional image data including a coronary artery region from the memory circuitry 140.

Next, the processing circuitry 110 automatically extracts anatomical structures from the three-dimensional image data (step S003). For example, as shown in FIG. 5 B, based on the anatomical structure of the coronary arteries, the processing circuitry 110 extracts the right coronary artery (RCA), the left circumflex coronary (LCX) and the left anterior descending coronary artery (LAD) from the acquired three-dimensional image data.

Next, the processing circuitry 110, for example, receives a designation for a region of interest from the surgeon, or receives a designation for a region of interest and a region of non-interest from the surgeon, and sets a region of interest to be observed as well as a region of non-interest that is different from the region of interest in the extracted anatomical structure (step S005).

Figure 5B:
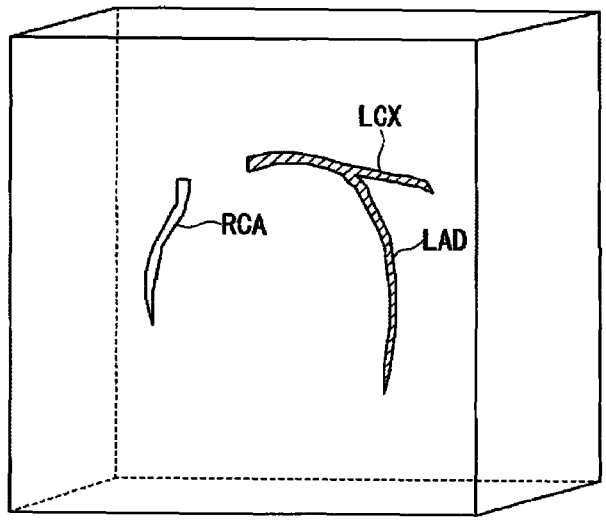
FIG. 5B is an explanatory view illustrating that a right coronary artery, a left circumflex coronary and a left anterior descending coronary artery are extracted from acquired three-dimensional image data based on the anatomical structure of the coronary arteries.

In the case of the coronary arteries, in main cases observation is mainly centered on the right coronary artery RCA, the left circumflex coronary LCX, and the left anterior descending coronary artery LAD. For example, in the case of checking narrowing of the right coronary artery RCA, the surgeon designates the right coronary artery RCA as the region of interest and designates the left circumflex coronary LCX and the left anterior descending coronary artery LAD as regions of non-interest. Upon accepting these designations of the surgeon, the processing circuitry 110 sets the right coronary artery RCA as a region of interest to be observed, and sets the left circumflex coronary LCX and the left anterior descending coronary artery LAD as regions of non-interest. In FIG. 5B, the left circumflex coronary LCX and the left anterior descending coronary artery LAD that are set as regions of non-interest are indicated by hatching.

Next, the processing circuitry 110 automatically determines the trajectory of the C-arm 26 based on a relative positional relationship between the region of interest and the region(s) of non-interest (step S007). In this case, the processing circuitry 110 generates an optimal trajectory map showing the trajectory of the C-arm 26 based on the relative positional relationship between the right coronary artery RCA as the region of interest and the left circumflex coronary LCX and the left anterior descending coronary artery LAD as the regions of non-interest.

In this case, generation of an optimal trajectory map is performed by adjusting a standard trajectory map (angle map) that is set as the initial setting or standard setting of the X-ray diagnostic apparatus 10, and generating an optimal trajectory map that is adapted to the specific shape of the coronary arteries of the patient P. Because the standard trajectory map is a trajectory map that is constructed as a database from data such as a large number of past imaging results, and is not a trajectory map that is adapted to the specific shape of the coronary arteries of the patient P, the standard trajectory map does not necessarily provide the optimal trajectory for the patient P. A more specific method for generating the optimal trajectory map is described hereunder referring to FIG. 6A, FIG. 6B, FIG. 7 and FIG. 8.

In the following description, it is assumed that the trajectory map that is set in advance as the standard setting is not the optimal trajectory map.

Figure 6A:
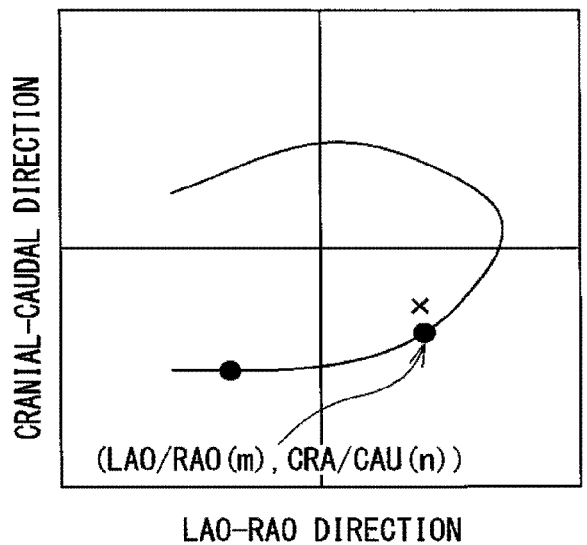
FIG. 6A is a view exemplifying a non-optimal trajectory map that is set in advance as a standard setting in the X-ray diagnostic apparatus according to the present embodiment.

FIG. 6A is a view illustrating an example of a non-optimal trajectory map that is set in advance as a standard setting in the X-ray diagnostic apparatus 10 according to the present embodiment. On the other hand, FIG. 6B is a view illustrating an example of an optimal trajectory map that is determined based on the relative positional relationship between a region of interest and a region of non-interest in step S007, which is an optimal trajectory map that is generated by being adapted to the specific shape of the coronary arteries of the patient P that is the imaging subject.

Figure 6B:
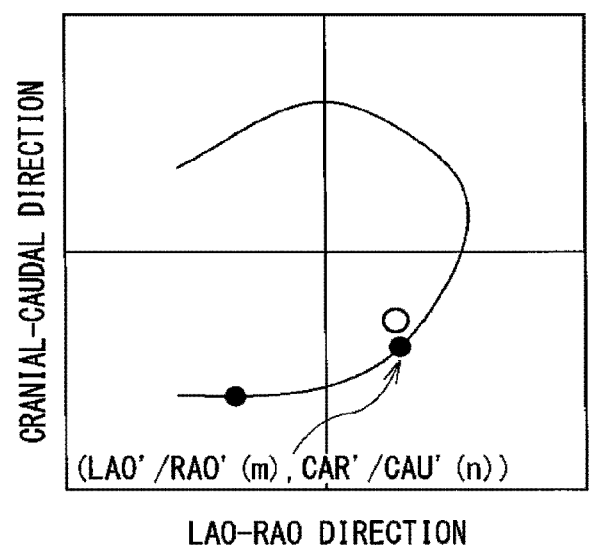
FIG. 6B is a view exemplifying an optimal trajectory map that is determined based on a relative positional relationship between a region of interest and a region of non-interest in step S007.

The abscissa axis (LAO (Left Anterior Oblique)-RAO (right anterior oblique) direction: horizontal direction) in FIG. 6A and FIG. 6B indicates the imaging angle of the C-arm 26 when moving to capture images of the patient P from the horizontal direction of the patient P in FIG. 1. Further, the ordinate axis (cranial-caudal direction) in FIG. 6A and FIG. 6B indicates the imaging angle of the C-arm 26 when moving to capture images of the patient P from the vertical direction of the patient P in FIG. 1.

The present embodiment generates the optimal trajectory map shown in FIG. 6B based on the trajectory map shown in FIG. 6A that is previously set as a standard setting. That is, a trajectory of the C-arm 26 that is previously registered is adjusted based on the relative positional relationship between the region of interest and the region(s) of non-interest, to thereby determine the optimal trajectory of the C-arm 26. In the following example, a method for generating the optimal trajectory map in a case where the right coronary artery RCA is taken as the region of interest is described.

In order to generate the optimal trajectory map, first the processing circuitry 110 virtually moves the C-arm 26 along a predetermined trajectory and determines whether or not the right coronary artery RCA that is the region of interest overlaps with the left anterior descending coronary artery LAD and the left circumflex coronary LCX that are regions of non-interest.

For example, first, the processing circuitry 110 virtually moves the C-arm 26 along the trajectory of the trajectory map (FIG. 6A) that is set in advance as the standard setting (hereunder, this trajectory is called "trajectory 1").

Based on the movable range of the C-arm 26, the processing circuitry 110 projects the right coronary artery RCA (region of interest) shown in FIG. 5B onto a two-dimensional image, and associates the angle at which the right coronary artery RCA is projected (projection angle) and the projection image (projection image 1) of the right coronary artery RCA and holds the associated information.

Figure 7:
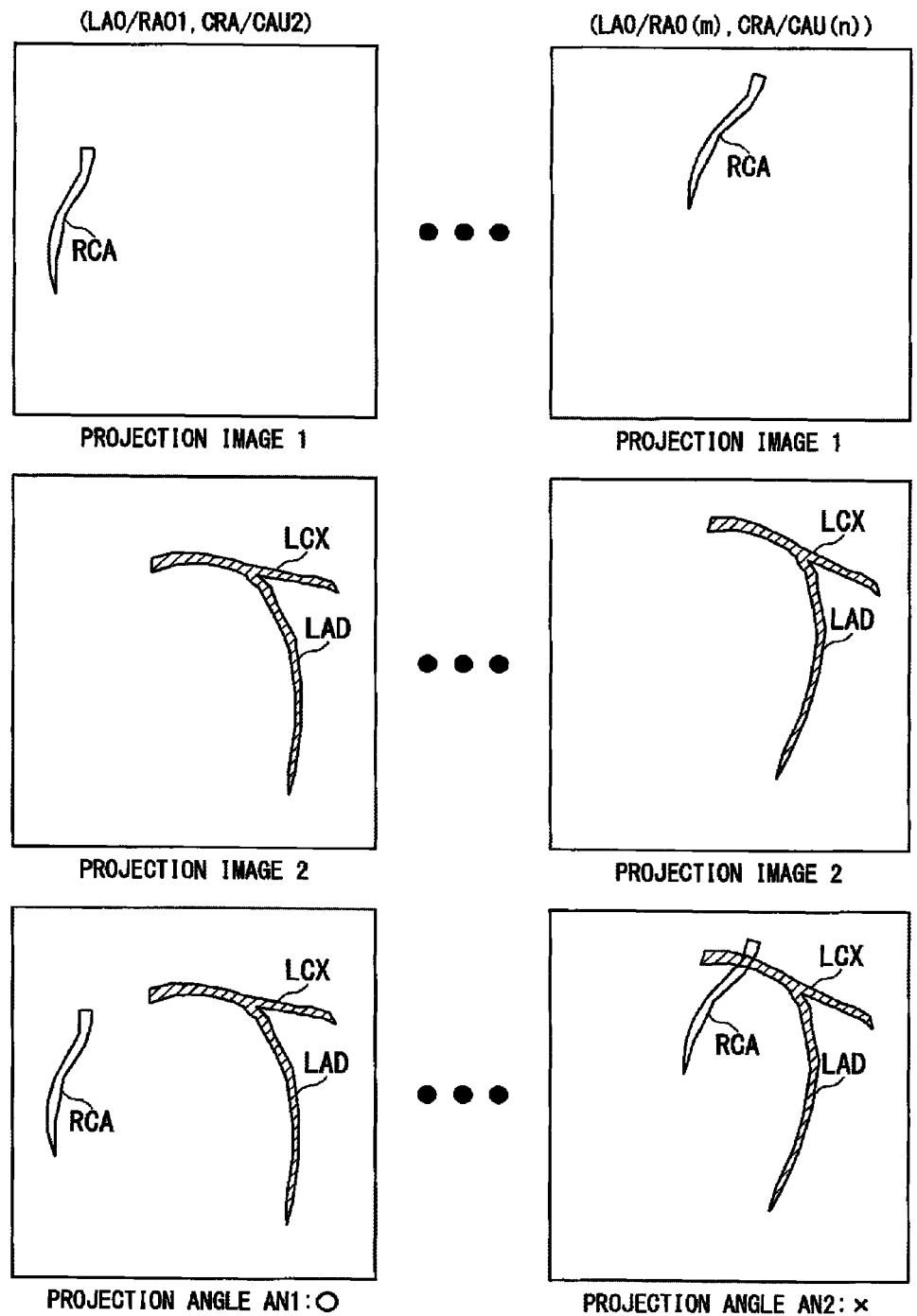
FIG. 7 is a schematic diagram illustrating an example in which a trajectory does not become the optimal trajectory during a process in which the processing circuitry according to the present embodiment generates an optimal trajectory map.

The views on the upper row in FIG. 7 illustrate examples of the projection image 1 of the right coronary artery RCA (region of interest) that are obtained at each projection angle. The view on the left in the upper row illustrates the projection image 1 that corresponds to a projection angle AN1. The view on the right in the upper row illustrates the projection image 1 that corresponds to a projection angle AN2.

Next, the processing circuitry 110 projects the left anterior descending coronary artery LAD and the left circumflex coronary LCX (both of which are regions of non-interest) shown in FIG. 5B onto a two-dimensional image, and associates the angle at which these regions are projected (projection angle) with the projection image (projection image 2) of the left anterior descending coronary artery LAD and the left circumflex coronary LCX and holds the associated information.

The views in the center row in FIG. 7 illustrate examples of the projection image 2 of the left anterior descending coronary artery LAD and the left circumflex coronary LCX (both of which are regions of non-interest) that are obtained at each projection angle. The view on the left in the center row illustrates the projection image 2 that corresponds to the projection angle AN1. The view on the right in the center row illustrates the projection image 2 that corresponds to the projection angle AN2.

Next, the processing circuitry 110 compares the projection image 1 and projection image 2 at each projection angle, and determines whether or not the right coronary artery RCA that is the region of interest overlaps with the left anterior descending coronary artery LAD and the left circumflex coronary LCX that are regions of non-interest.

In the example in FIG. 7, as shown in the views on the lower row in FIG. 7, at the projection angle AN2, when the projection image 1 and the projection image 2 are compared it is found that the right coronary artery RCA that is the region of interest overlaps with the left circumflex coronary LCX. Accordingly, the trajectory 1 that includes the projection angle AN2 will not be the optimal trajectory. That is, the processing circuitry 110 superimposes the projection image 1 onto the projection image 2, and determines whether or not the right coronary artery RCA that is the region of interest overlaps with the left anterior descending coronary artery LAD and the left circumflex coronary LCX. If the region of interest and a region of non-interest overlap, the trajectory will not be the optimal trajectory.

Incidentally, "×", since the region of interest overlaps with the non-interest region, trajectory 1 shows that not the optimal trajectory.

If it is determined that the trajectory 1 is not the optimal trajectory, the processing circuitry 110 performs the same processing as above with respect to a new trajectory 2 obtained by moving the trajectory by a predetermined amount from the trajectory 1, and determines whether or not the region of interest and a region of non-interest overlap. This processing is repeated until a trajectory with which the region of interest and a region of non-interest do not overlap is obtained.

Figure 8:
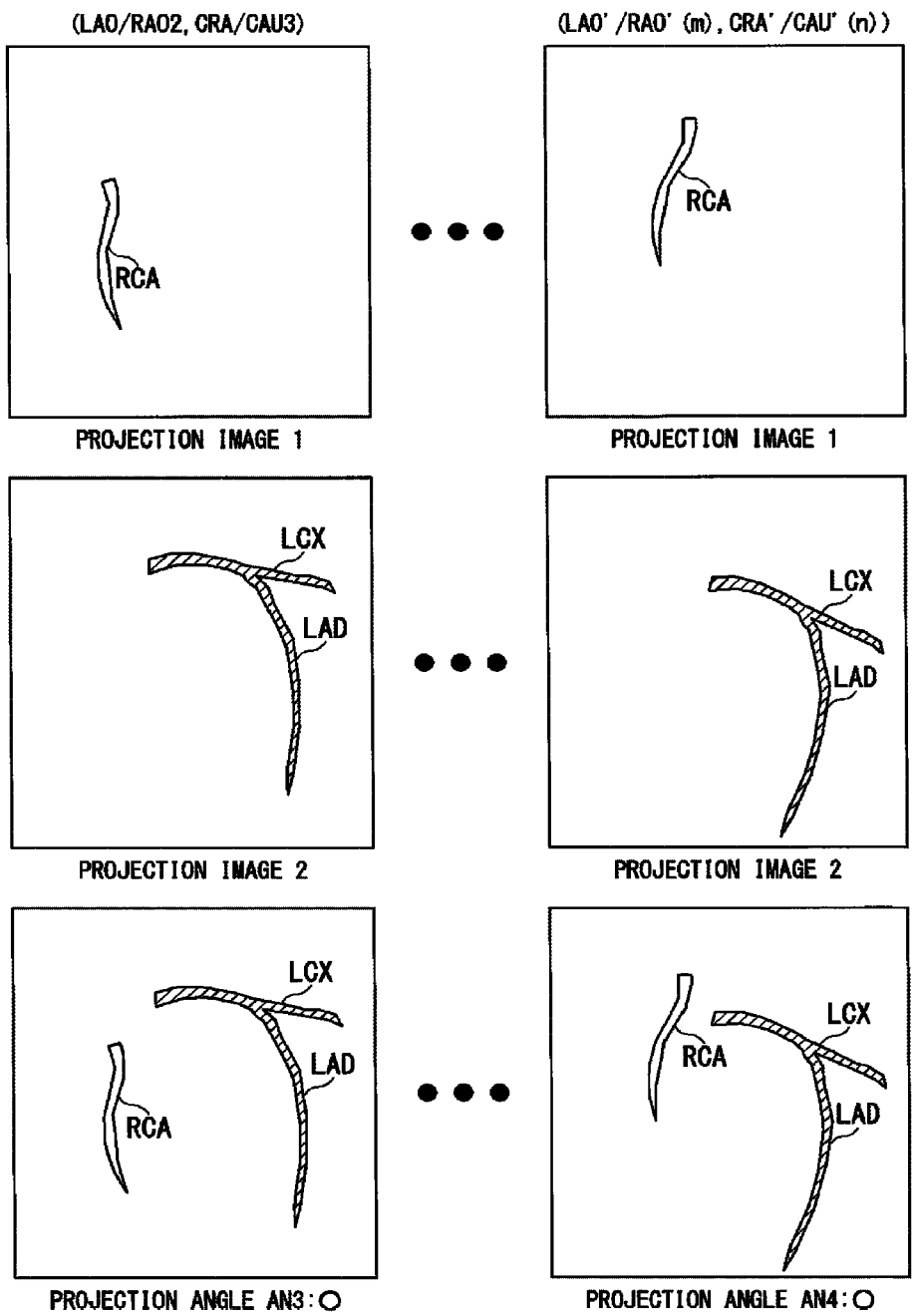
FIG. 8 is a schematic diagram illustrating an example in which a trajectory becomes the optimal trajectory during a process in which the processing circuitry according to the present embodiment generates an optimal trajectory map.

FIG. 8 is a schematic diagram illustrating an example in which, during a process in which the processing circuitry 110 according to the present embodiment generates an optimal trajectory map, the relevant trajectory is the optimal trajectory.

FIG. 8 illustrates an example in which the C-arm 26 moves according to the trajectory 2, and shows a projection image when an imaging angle on the trajectory 2 of the C-arm 26 is a projection angle AN3, and a projection image when the imaging angle is a projection angle AN4.

In this case, it is shown that, with respect to the trajectory 2 from the projection angle AN3 to the projection angle AN4, when the projection image 1 and the projection image 2 are compared it is found that the right coronary artery RCA that is the region of interest and the left anterior descending coronary artery LAD and the left circumflex coronary LCX that are regions of non-interest do not overlap, and hence the trajectory 2 is the optimal trajectory. Further, whether or not an imaging angle is an easily viewable angle can be determined by superimposing the projection image 1 onto the projection image 2.

Note that "O", since the region of interest does not overlap with the non-interest region, the trajectory 2 shows that the optimal trajectory.

Upon generating the optimal trajectory map (FIG. 6B) in which the right coronary artery RCA that is the region of interest and the left anterior descending coronary artery LAD and the left circumflex coronary LCX that are regions of non-interest do not overlap (step S007), the processing circuitry 110 sends the generated optimal trajectory map along with three-dimensional image data of the coronary artery region to the DF device 12, and ends the optimal trajectory map generation processing (step S009).

Note that, a method for calculating a trajectory map in which the right coronary artery RCA that is the region of interest and the left anterior descending coronary artery LAD and the left circumflex coronary LCX that are regions of non-interest do not overlap is not limited to this method. For example, a configuration may also be adopted in which, each time the projection angle is changed, it is simultaneously determined whether or not a projection image of the region of interest and a projection image of the region(s) of non-interest overlap.

Furthermore, a configuration may also be adopted so as to allow a certain amount of overlapping between the projection image of the region of interest and a projection image of the region(s) of non-interest. For example, a configuration may be adopted so as to generate an optimal trajectory map by determining the suitability of a trajectory based on a proportion that a region of interest occupies in an overlapping portion when projection images are superimposed.

Rotational Imaging Processing

Next, processing whereby the X-ray diagnostic apparatus 10 according to the first embodiment controls the rotational trajectory of the C-arm 26 based on the optimal trajectory map generated by the medical image processing apparatus 100 and performs rotational imaging will be described.

Figure 9:
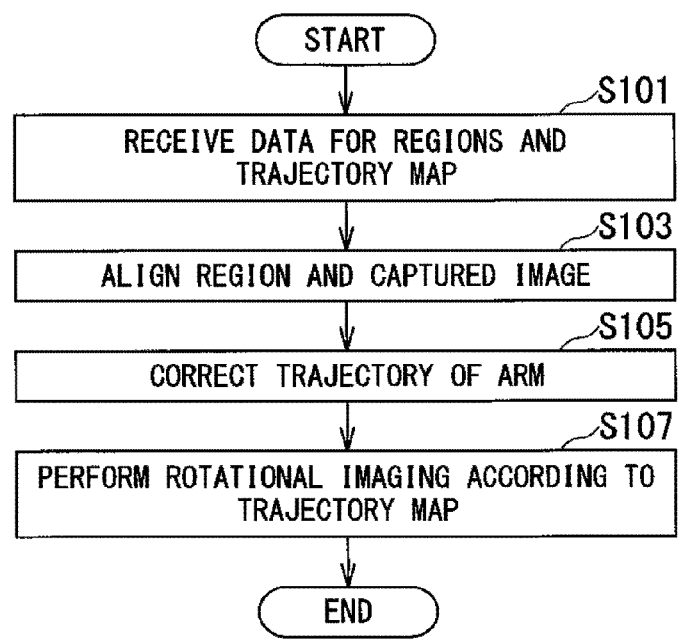
FIG. 9 is a flowchart illustrating processing in which, when imaging coronary arteries of a patient, the processing circuitry of the X-ray diagnostic apparatus according to the first embodiment rotationally controls the C-arm at the optimal trajectory and performs rotational imaging.
Figure 10A:
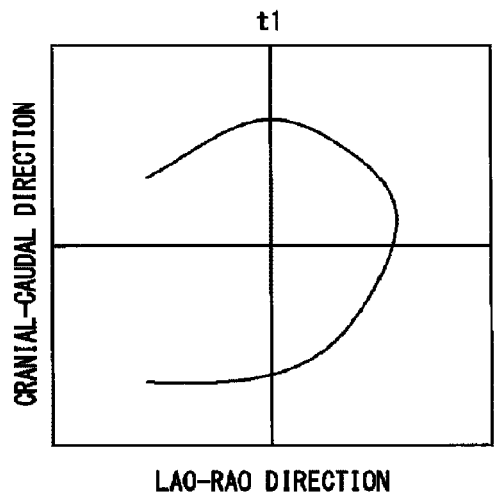
FIG. 10A to FIG. 10D are schematic diagrams illustrating respective trajectories in a case where a medical image processing apparatus according to a second embodiment generates respective optimal trajectory maps based on four items of volume data in accordance with four temporal phases.
Figure 10B:
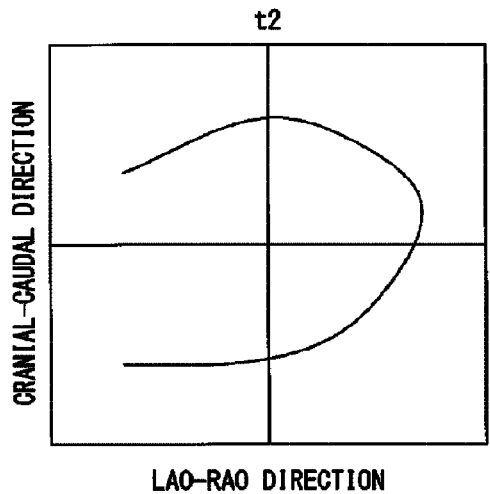
Figure 10C:
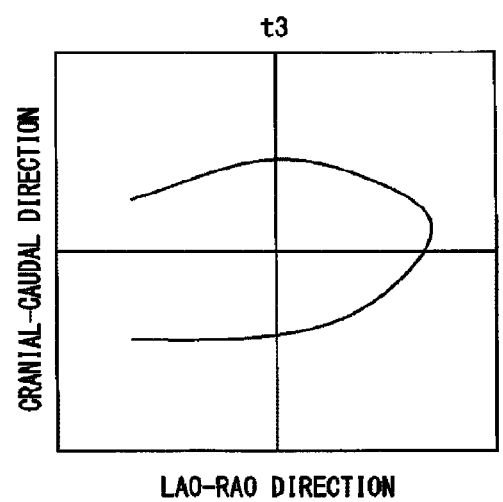
Figure 10D:
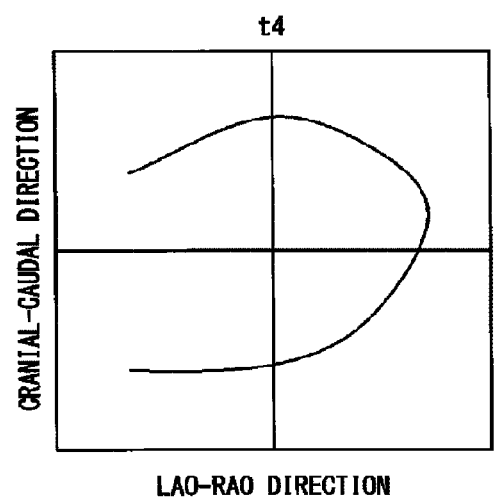

FIG. 9 is a flowchart illustrating processing whereby, at a time of imaging the coronary arteries of the patient P, the processing circuitry 41 of the X-ray diagnostic apparatus 10 according to the first embodiment rotationally controls the C-arm 26 along the optimal trajectory and performs rotational imaging.

First, the processing circuitry 41 of the X-ray diagnostic apparatus 10 according to the first embodiment receives three-dimensional image data of the coronary artery region and the optimal trajectory map from the processing circuitry 110 of the medical image processing apparatus 100 via the network N, and stores the three-dimensional image data of the coronary artery region and the optimal trajectory map in the first memory circuitry 42 (step S101).

Next, the processing circuitry 41 reads out a program corresponding to the alignment function from the first memory circuitry 42, and performs alignment between captured images of the patient P that are captured from a plurality of directions and a region of three-dimensional image data of the coronary artery region that is received (step S103).

An X-ray angiographic image or a contrast image that is captured by the X-ray diagnostic apparatus 10 can be used as the captured images. The processing circuitry 41 performs alignment between a region of the coronary arteries that is shown by the three-dimensional image data of the coronary artery region and the captured images, using captured images that are X-ray angiographic images or contrast images stored in the second memory circuitry 51.

Note that, with respect to the captured images used for alignment, because the accuracy can be increased as the number of captured images increases, alignment is performed based on a large number of captured images that are obtained by capturing images of the patient P from a plurality of directions and a region of the coronary arteries that is an anatomical structure.

The processing circuitry 41 corrects the optimal trajectory map and corrects the rotational trajectory of the C-arm 26 by an amount corresponding to an amount by which the three-dimensional image data of the coronary artery region is aligned with respect to the captured images, that is, based on a displacement amount between the three-dimensional image data of the coronary artery region before alignment and the captured images (step S105). For example, a transformation matrix can be applied as the method for correcting.

The processing circuitry 41 controls the rotational trajectory of the C-arm 26 and executes rotational imaging in accordance with the trajectory (optimal trajectory map) of the C-arm 26 that is determined by the medical image processing apparatus 100 (step S107).

For example, while rotating the C-arm 26, the processing circuitry 41 generates a fluoroscopic image by controlling the image processing circuitry 52, and displays the generated fluoroscopic image on the display 54. When rotational imaging by means of the C-arm 26 ends, the processing circuitry 41 ends the rotational imaging processing.

As described above, the X-ray diagnostic apparatus 10 according to the first embodiment extracts an anatomical structure from three-dimensional image data that is volume data, and sets, in the extracted anatomical structure, a region of interest to be observed and a region of non-interest that is different from the region of interest.

In the case of the present embodiment, since a configuration is adopted so as to determine the trajectory of the C-arm 26 based on the relative positional relationship between a region of interest and a region of non-interest using an anatomical structure of volume data, the rotational trajectory of the C-arm 26 can be determined with higher accuracy. The X-ray diagnostic apparatus 10 according to the present embodiment can then control the rotational trajectory of the C-arm 26 in accordance with the trajectory (optimal trajectory map) of the C-arm 26 that is determined.

Thus, according to the X-ray diagnostic apparatus 10 of the present embodiment, even in the case of rotationally imaging a region of interest such as the coronary arteries, an optimal angle of the C-arm 26 can be automatically determined.

Note that, although in the present embodiment a configuration is adopted so as to generate an optimal trajectory map in the medical image processing apparatus 100, a configuration may also be adopted in which functions of the medical image processing apparatus 100 are incorporated into the DF device 12 of the X-ray diagnostic apparatus 10 so as to generate an optimal trajectory map in the DF device 12.

In this case, since an optimal trajectory map can be generated in the DF device 12 by acquisition of volume data or volume data of an anatomical structure via the network N by the X-ray diagnostic apparatus 10, generation of an optimal trajectory map can be realized in the same manner.

Second Embodiment

According to the first embodiment, the medical image processing apparatus 100 is configured to generate an optimal trajectory map based on volume data for a certain temporal phase. According to the second embodiment, the medical image processing apparatus 100 is configured to generate an optimal trajectory map corresponding to a plurality of temporal phases based on volume data for a plurality of temporal phases.

For example, the processing circuitry 110 of the medical image processing apparatus 100 extracts chronological anatomical structure positions from volume data in time series that is captured for a plurality of temporal phases. By this means, the processing circuitry 110 can determine the respective trajectories of the C-arm 26 at the chronological anatomical structure positions based on the relative positional relationship between a region of interest and a region of non-interest.

Cardiac motion is broadly divided into a diastole and a systole. The diastole is a temporal phase in which the left and right ventricles expand. Further, the heartbeat is related with valvular motion, and the form of the ventricles or atria changes in accordance therewith. For example, the positions or shapes of the ventricles or atria change according to temporal phases such as the isometric contraction phase, maximum ejection phase, reduced ejection phase, and expansion preparation phase, and the positions of the coronary arteries also change in accompaniment therewith. Therefore, by generating an optimal trajectory map for each temporal phase of a plurality of temporal phases that are in chronological order, an optimal trajectory map for a time of imaging a desired cardiac temporal phase can be obtained.

FIG. 10A to FIG. 10D are schematic diagrams illustrating respective trajectories in a case where, based on four items of volume data for four temporal phases, the medical image processing apparatus 100 according to the second embodiment generates an optimal trajectory map for each of the items of volume data.

In FIG. 10A to FIG. 10D, examples of optimal trajectory maps are illustrated that are respectively generated in accordance with respective heartbeat fluctuations at four temporal phases. Note that, as one example, the four temporal phases are illustrated in time series in alphabetical order from FIG. 10A to FIG. 10D (corresponds to the order of t1 to t4).

In addition, in the second embodiment, the following utilization forms are conceivable by utilizing the generation of respective optimal trajectory maps based on respective items of volume data for a plurality of temporal phases.

First Utilization Form

A form will now be described in which electrocardiogram synchronization (ECG synchronization) is used to perform fixed fluoroscopy with respect to a region of interest which it is desired to observe of the patient P according to the second embodiment.

The term "fixed fluoroscopy" refers to a fluoroscopy method that fixes a region of interest which it is desired to observe and performs fluoroscopic imaging, and is a method that fixes the position of the C-arm 26 and consecutively observes a plurality of temporal phases. At such time, the angle of the C-arm 26 is finely adjusted in real time according to changes in the region of interest in the each of the plurality of temporal phases.

In this case, the processing circuitry 110 uses ECG synchronization to synchronize three-dimensional image data for the patient P with temporal phases of a coronary artery region of the patient P. The processing circuitry 110 may generate the three-dimensional image data a plurality of times in time series, or may perform image interpolation processing based on a plurality of items of three-dimensional image data to thereby generate a plurality of items of three-dimensional image data in time series for the patient P.

Note that, since imaging by the X-ray CT apparatus is accompanied by radiation exposure, it is preferable to perform image interpolation processing on three-dimensional image data to generate a plurality of items of three-dimensional image data in time series.

Thus, the processing circuitry 110 sets a region of interest in each of the plurality of items of three-dimensional image data in time series for the patient P, and finely adjusts the imaging angle of the C-arm 26 so as to continue the fixed fluoroscopy even if a chronological change in the position or shape of the region of interest occurs. That is, the processing circuitry 110 synchronizes the rotational trajectory of the C-arm 26 with the heartbeat, and generates a trajectory for controlling the position of the C-arm 26 with respect to the region of interest in real time.

Figure 11A:
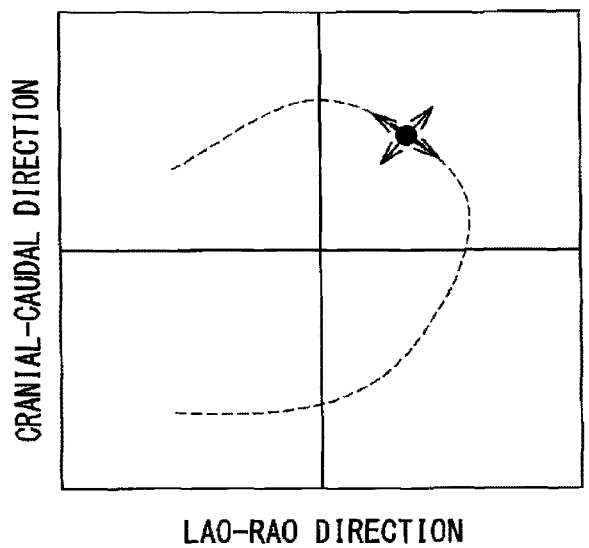
FIG. 11A and FIG. 11B are schematic diagrams illustrating a concept of the medical image processing apparatus according to the second embodiment finely adjusting an imaging angle of a C-arm on an optimal trajectory map in accordance with heartbeat fluctuations by means of ECG synchronization.
Figure 11B:
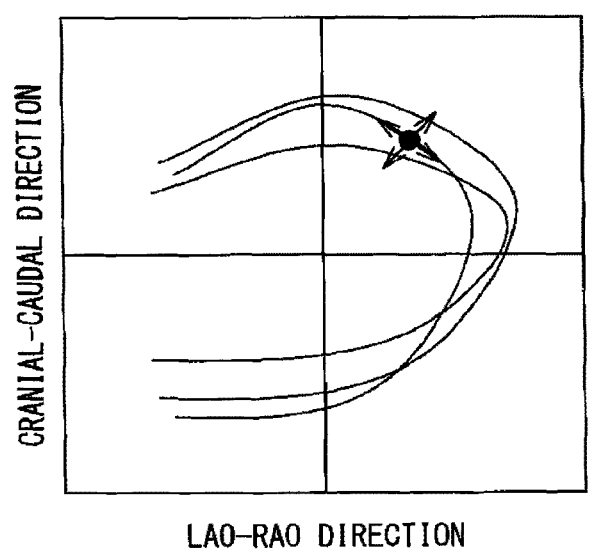

FIG. 11A and FIG. 11B are schematic diagrams that illustrate the concept of the medical image processing apparatus 100 according to the second embodiment finely adjusting an imaging angle of the C-arm 26 in the optimal trajectory map in accordance with heartbeat fluctuations using ECG synchronization.

As shown in FIG. 11A, the processing circuitry 110 finely adjusts the imaging angle in the optimal trajectory map in accordance with heartbeat fluctuations. For example, in a case where the right coronary artery RCA is adopted as the region of interest for fixed fluoroscopy by the processing circuitry 110, the imaging angle varies little by little in time series in accordance with heartbeat fluctuations.

Therefore, to perform fixed fluoroscopy of the right coronary artery RCA as the region of interest, the processing circuitry 110 identifies a position and an imaging direction at which the right coronary artery RCA is easily viewable, and finely adjusts the imaging angle of the C-arm 26 chronologically in accordance with the chronological changes in the heartbeat.

FIG. 11B is a schematic diagram illustrating the concept of finely adjusting the imaging angle illustrated in FIG. 11A. The processing circuitry 110 can finely adjust the imaging angle in the optimal trajectory map in accordance with a change in temporal phases of a plurality of temporal phases. The processing circuitry 110 uses respective optimal trajectory maps for each of the plurality of temporal phases to finely adjust the imaging angle so as to perform fixed fluoroscopy with respect to the right coronary artery RCA that is the region of interest.

By this means, without needing to perform a special operation, the surgeon can obtain real-time fluoroscopic images by fixed fluoroscopy of the region of interest at the optimal imaging angle of the C-arm 26.

Second Utilization Form

A form will now be described in which ECG synchronization is used to perform rotational imaging with respect to a region of interest which it is desired to observe of the patient P according to the second embodiment.

By using ECG synchronization, the processing circuitry 110 synchronizes the three-dimensional image data for the patient P with a temporal phase of a coronary artery region of the patient P. In this case also, similarly to the case described above, for example, the processing circuitry 110 may generate three-dimensional image data a plurality of times in time series, or may perform image interpolation processing based on a plurality of items of three-dimensional image data to thereby generate a plurality of items of three-dimensional image data in time series for the patient P.

The processing circuitry 110 sets a region of interest in each of the plurality of items of three-dimensional image data in time series for the patient P, and controls the imaging angle of the C-arm 26 chronologically so that the region of interest can be rotationally imaged. That is, the processing circuitry 110 synchronizes temporal phases of the chronological anatomical structure and temporal phases that are to be imaged, and generates a trajectory that controls the rotational trajectory of the C-arm 26 so as to capture images of the region of interest in the temporal phases that are to be imaged.

Figure 12A:
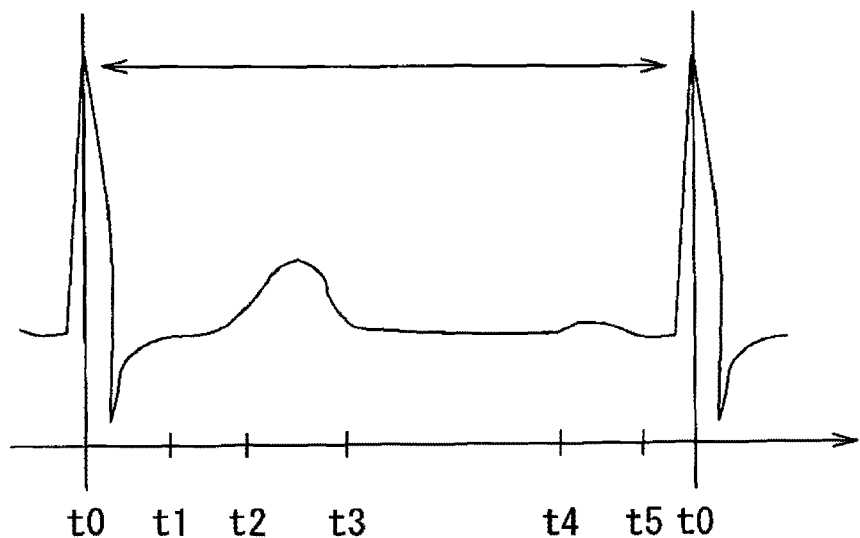
FIG. 12A and FIG. 12B are schematic diagrams illustrating a concept of the medical image processing apparatus according to the second embodiment setting an imaging angle of the C-arm to an optimal setting in accordance with heartbeat fluctuations by means of ECG synchronization.
Figure 12B:
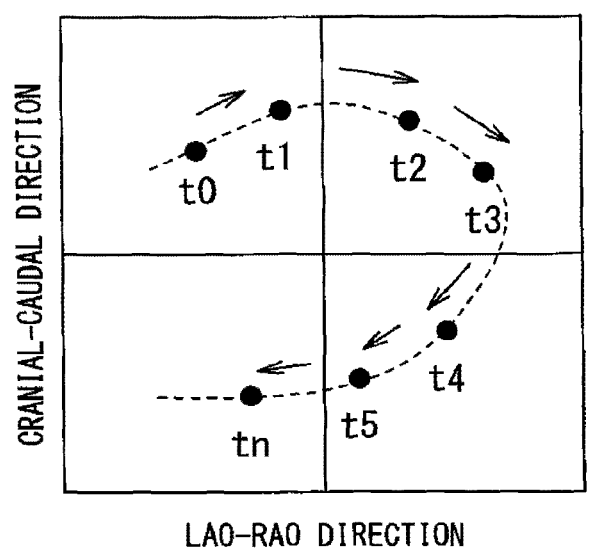

FIG. 12A and FIG. 12B are schematic diagrams that illustrate the concept of the medical image processing apparatus 100 according to the second embodiment setting the imaging angle of the C-arm 26 to an optimal setting in accordance with heartbeat fluctuations by means of ECG synchronization.

As shown in FIG. 12A and FIG. 12B, the processing circuitry 110 is configured to synchronize the imaging angle of the C-arm 26 with heartbeat fluctuations, and change the imaging angle in accordance with the temporal phase that is to be imaged.

FIG. 12A illustrates an electrocardiographic waveform that illustrates an example of the cycle of the heartbeat of the patient P. FIG. 12B illustrates imaging angles at which the C-arm 26 performs rotational imaging at a predetermined temporal phase cycle in the electrocardiographic waveform shown in FIG. 12A.

The temporal phase of the optimal trajectory map and the imaging angle in FIG. 12B will now be described using separate drawings.

FIG. 13A to FIG. 13D are conceptual diagrams illustrating a concept of the medical image processing apparatus 100 according to the second embodiment setting imaging angles at which to perform rotational imaging.

The imaging angles shown in FIG. 12B show the imaging angles at the respective temporal phases. These imaging angles are set based on imaging angles of the optimal trajectory map for the respective temporal phases shown in FIG. 13A to FIG. 13D.

For example, FIG. 13A to FIG. 13D show optimal trajectory maps at four temporal phases from a t1 to a t4, and show the respective angles when performing rotational imaging for the respective temporal phases. That is, in FIG. 13A, an angle of the rotational imaging when the temporal phase is t1 is indicated by an imaging angle ANt1. The imaging angle ANt1 corresponds to an imaging angle at t1 in FIG. 12B. Further, in FIG. 13B, an angle of the rotational imaging when the temporal phase is t2 is indicated by an imaging angle ANt2. The imaging angle ANt2 corresponds to an imaging angle at t2 in FIG. 12B.

Figure 13A:
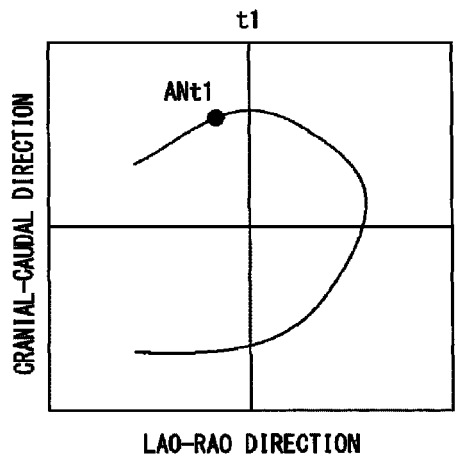
FIG. 13A to FIG. 13D are conceptual diagrams illustrating a concept of the medical image processing apparatus according to the second embodiment setting an imaging angle at which to perform rotational imaging.
Figure 13B:
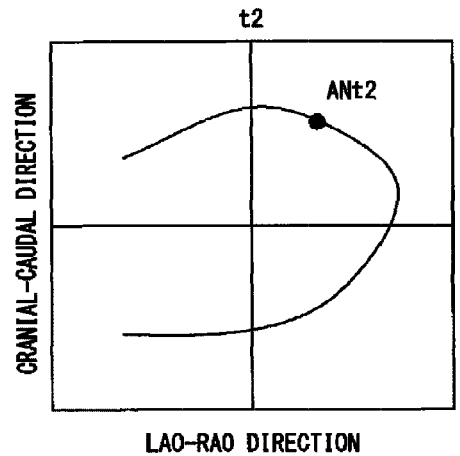
Figure 13C:
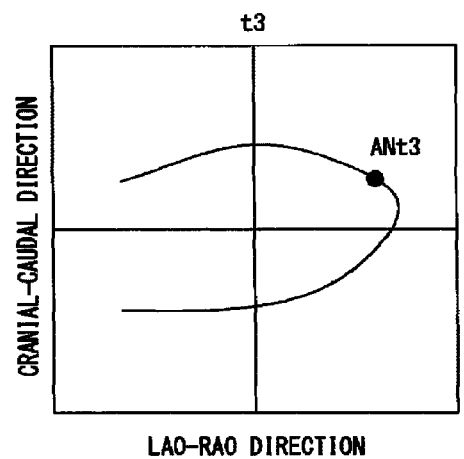
Figure 13D:
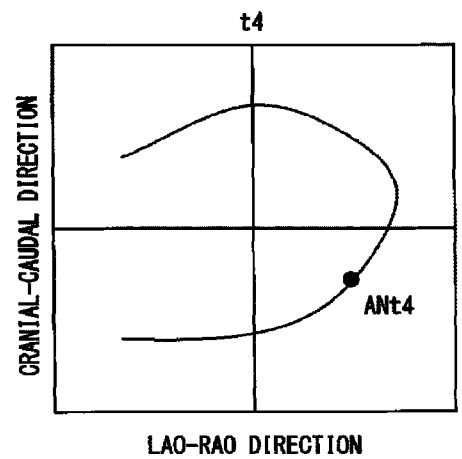

Likewise, in FIG. 13C, an angle of the rotational imaging when the temporal phase is t3 is indicated by an imaging angle ANt3. The imaging angle ANt3 corresponds to an imaging angle at t3 in FIG. 12B. Further, in FIG. 13D, an angle of the rotational imaging when the temporal phase is t4 is indicated by an imaging angle ANt4. The imaging angle ANt4 corresponds to an imaging angle at t4 in FIG. 12B.

Thus, the processing circuitry 110 can capture images of a region of interest of the patient P at an optimal imaging angle of the C-arm 26 that is synchronized with chronological changes in the heartbeat of the patient P.

By this means, without needing to perform a special operation, the surgeon can perform rotational imaging at optimal imaging angles of the C-arm 26 as ECG-synchronized imaging, and obtain captured images.

Note that, in the first and second embodiments configurations are adopted so as to generate optimal trajectory maps using three-dimensional image data acquired with another modality device such as a CT apparatus. Instead of acquiring three-dimensional image data from another modality device, three-dimensional image data may be generated by the X-ray diagnostic apparatus 10. For example, a configuration may be adopted so as to generate three-dimensional image data based on rotational DSA (digital subtraction angiography) images of the patient that are acquired by rotating the C-arm 26.

By this means, the X-ray diagnostic apparatus 10 can create an optimal trajectory map in the DF device 12 thereof. In this case, because the correlation between an X-ray angiographic image and an optimal trajectory map is already obtained, the alignment processing described in the first embodiment can be omitted.

As described above, according to the medical image processing apparatus 100 of at least one embodiment, in the case of performing rotational imaging with respect to a region of interest such as a coronary artery, the medical image processing apparatus 100 or the X-ray diagnostic apparatus 10 can automatically determine the optimal angle of the C-arm 26.

Although several embodiments of the present invention have been described above, these embodiments have been presented by way of example only, and are not intended to limit the scope of the inventions. Indeed, the embodiments described herein may be embodied in a variety of other forms; furthermore, various omissions, substitutions and changes in the form of the embodiments described herein may be made without departing from the gist of the invention. These embodiments and the modifications thereof are included within the scope and gist of the invention, and are also included in the scope of the inventions described in the accompanying claims and their equivalents.

What is claimed is:

1. A medical image processing apparatus comprising:
a memory circuitry configured to store a program; and
a processing circuitry configured to read out the program from the memory circuitry and execute the program;
wherein the processing circuitry is configured to:
set a region of interest to be observed and a region of non-interest that is different to the region of interest based on volume data, and
determine a trajectory of an arm that holds an X-ray irradiator configured to irradiate X-rays and a detector configured to detect the X-rays that are irradiated, based on a relative positional relationship between the region of interest and the region of non-interest.

2. The medical image processing apparatus according to claim 1, wherein the processing circuitry is configured to:
control a rotational trajectory of the arm in accordance with the trajectory of the arm that is determined,
generate a fluoroscopic image, and cause the fluoroscopic image that is generated to be displayed on a display while rotating the arm.

3. The medical image processing apparatus according to claim 2, wherein the processing circuitry is configured to:
synchronize the rotational trajectory of the arm with a heartbeat, and
control a position of the arm with respect to the region of interest in real time.

4. The medical image processing apparatus according to claim 2, wherein the processing circuitry is configured to:
execute alignment between a captured image obtained by imaging an object from a plurality of directions and an anatomical structure in the volume data, and
correct the rotational trajectory of the arm using a difference between the captured image and the volume data that is obtained by the alignment.

5. The medical image processing apparatus according to claim 2, which is configured to acquire any of the volume data, data of the anatomical structure and data of a trajectory of the arm via a network, and
control the rotational trajectory of the arm.

6. The medical image processing apparatus according to claim 1, wherein the processing circuitry is configured to:
project the region of interest and the region of non-interest onto a two-dimensional image,
calculate an imaging angle at which a projection image of the region of interest and a projection image of the region of non-interest do not overlap, and
determine a trajectory of the arm based on the imaging angle at which the projection image of the region of interest and the projection image of the region of non-interest do not overlap.

7. The medical image processing apparatus according to claim 1, wherein the processing circuitry is configured to:
determine a trajectory of the arm by adjusting a trajectory of the arm that is previously registered, based on a relative positional relationship between the region of interest and the region of non-interest.

8. The medical image processing apparatus according to claim 1, wherein the processing circuitry is configured to:
extract an anatomical structure from the volume data, and
set the region of interest and the region of non-interest using the anatomical structure that is extracted.

9. The medical image processing apparatus according to claim 8, wherein a vascular region is adopted as a subject of the anatomical structure.

10. The medical image processing apparatus according to claim 1, wherein the processing circuitry is configured to:
extract a chronological anatomical structure from volume data in time series that is obtained by imaging of a plurality of temporal phases, and
determine a position or a trajectory of the arm corresponding to the plurality of temporal phases based on a relative positional relationship between the region of interest and the region of non-interest in the plurality of temporal phases.

11. The medical image processing apparatus according to claim 10, wherein the processing circuitry is configured to:
synchronize a temporal phase of the chronological anatomical structure and a temporal phase to be imaged, and
control the rotational trajectory of the arm so as to image the region of interest in the temporal phase to be imaged.

12. The medical image processing apparatus according to claim 10, wherein:
the volume data in time series is interpolated between temporal phases of the plurality of temporal phases; and
the processing circuitry is configured to:
extract the chronological anatomical structure from the volume data in time series that is interpolated, and
determine a trajectory of the arm based on a relative positional relationship between the region of interest and the region of non-interest in the chronological anatomical structure that is interpolated.

13. The medical image processing apparatus according to claim 1, wherein the volume data is data that is imaged in advance by an X-ray CT apparatus.

14. The medical image processing apparatus according to claim 1, wherein the processing circuitry is configured to accept settings for the region of interest and the region of non-interest based on an operation of a user.

15. An X-ray diagnostic apparatus comprising:
an X-ray irradiator configured to irradiate X-rays;
a detector configured to detect the X-rays that are irradiated;
an arm configured to hold the X-ray irradiator and the detector; and
a processing circuitry configured to read out and execute a program;
wherein the processing circuitry is configured to:
set a region of interest to be observed and a region of non-interest that is different to the region of interest based on volume data,
determine a trajectory of the arm based on a relative positional relationship between the region of interest and the region of non-interest, and
control a rotational trajectory of the arm in accordance with the trajectory of the arm that is determined.

16. The X-ray diagnostic apparatus according to claim 15, wherein the processing circuitry is configured to:
generate a fluoroscopic image and cause the fluoroscopic image that is generated to be displayed on a display while rotating the arm.

17. The X-ray diagnostic apparatus according to claim 15, wherein the processing circuitry is configured to:
synchronize the rotational trajectory of the arm with a heartbeat, and
control a position of the arm with respect to the region of interest in real time.

18. The X-ray diagnostic apparatus according to claim 15, wherein the processing circuitry is configured to:
perform alignment between a captured image obtained by imaging an object from a plurality of directions and an anatomical structure in the volume data, and
correct the rotational trajectory of the arm using a difference between the captured image and the volume data that is obtained by the alignment.

* * * * *